United States Patent [19]

Garner et al.

[11] Patent Number: 5,429,952
[45] Date of Patent: Jul. 4, 1995

[54] MARKING OF PRODUCTS TO ESTABLISH IDENTITY AND SOURCE

[75] Inventors: Ronald C. Garner, Sand Hutton; Carl N. Martin, Thorganby; Michael J. Wraith, Sittingbourne; David W. Britton, all of Faversham, Great Britain

[73] Assignee: Biocode, Inc., Barnstable, Mass.

[21] Appl. No.: 109,938

[22] Filed: Aug. 20, 1993

Related U.S. Application Data

[63] Continuation-in-part of Ser. No. 571,633, Sep. 10, 1990, abandoned, and a continuation-in-part of Ser. No. 18,477, Feb. 16, 1993, abandoned, which is a continuation of Ser. No. 765,401, Sep. 24, 1991, abandoned, which is a continuation of Ser. No. 302,278, Jan. 27, 1989, abandoned.

[30] Foreign Application Priority Data

Feb. 2, 1988 [GB] United Kingdom ............... 8802237
Feb. 8, 1988 [GB] United Kingdom ............... 8802838

[51] Int. Cl.$^6$ ..................... G01N 33/53; G01N 33/26
[52] U.S. Cl. ..................... 436/518; 436/2; 436/29; 436/822
[58] Field of Search ............ 436/518, 501, 543, 2, 436/8, 20, 22, 23, 24, 29, 822; 435/9; 283/95, 96, 97

[56] References Cited

U.S. PATENT DOCUMENTS

| | | |
|---|---|---|
| 4,341,758 | 7/1982 | Sakakibara et al. ............ 436/534 |
| 4,770,853 | 9/1988 | Bernstein ..................... 422/58 |
| 4,859,611 | 8/1989 | Groopman et al. ............ 436/513 |

FOREIGN PATENT DOCUMENTS

| | | |
|---|---|---|
| 0260829 | 3/1988 | European Pat. Off. . |
| 0327163 | 8/1989 | European Pat. Off. . |
| 8802237 | 2/1988 | United Kingdom . |
| 8802838 | 2/1988 | United Kingdom . |
| 8706383 | 10/1987 | WIPO . |
| 88/09798 | 12/1988 | WIPO . |
| 89/07272 | 8/1989 | WIPO . |

OTHER PUBLICATIONS

Regulations for the Quartermaster Service in the Army and the Home Guard, Coloring of Petrol at Military Petrol Stations, BIH 2–011 (Oslo, May 15, 1975).
Saunders et al, "Double–Antibody Solid–Phase Enzyme Immunoassay for the Detection of Staphylococcal Enterotoxin A", Appl. Environ. Microbiol., 34(5):518–522 (Nov. 1977).
Dixon et al, "Hybridoma Cell Line Production of a Specific Monoclonal Antibody to Mycotoxins Zearalenone and α-Zearalenol", J. Agric. Food Chem., 35:122–126 (1987).
Wrath et al, "Development of Immunoassay Methods for Pyrothroid Insecticides", 6th Int. Congress of Pesticide Chem., Aug. 10–15, 1986.
Voller et al;., Manual of Clinical Laboratory Immunology, Editors: Rose et al., Published 1986, pp. 99–109.
Kelley, Marian M. et al., J. Agric. Food Chem., vol. 33, pp. 962–965 (1985).
Newsome, William H., J. Agric. Food Chem., vol. 33, pp. 528–530 (1985).
Wie, Siong I. et al., J. Agric. Food Chem., vol. 30, pp. 949–957 (1982).
Monroe, D., Analytical Chemistry, vol. 56, pp. 920A–931A (1984).
Siddle, K., Alternative Immunoassays, (W. P. Collins, Ed.), pp. 13–37 (1985).

*Primary Examiner*—Carol E. Bidwell
*Attorney, Agent, or Firm*—Fish & Richardson

[57] ABSTRACT

In general, the invention features a method of marking a product for identification in which a low molecular weight hapten is associated with the product as a marker, where the hapten is non-deleterious to the product, inert with respect to the product, and not already associated with the product.

10 Claims, 4 Drawing Sheets

MARKING OF PRODUCTS TO ESTABLISH IDENTITY AND SOURCE

BACKGROUND OF THE INVENTION

This application is a continuation-in-part of U.S. Ser. No. 07/571,633, filed Sep. 10, 1990 by Garner et al., now abandoned, which in turn claims priority from PCT/GB89/00121, filed Feb. 8, 1989, which in turn claims priority from GB 88 02838, filed Feb. 8, 1988; this application is also a continuation-in-part of U.S. Ser. No. 08/018,477, filed Feb. 16, 1993 by Wraith et al., now abandoned, which is a continuation of U.S. Ser. No. 07/765,401, filed Sep. 24, 1991, now abandoned, which is a continuation of U.S. Ser. No. 07/302,278, filed Jan. 27, 1989, now abandoned, which in turn claims priority from GB 88 02237, filed Feb. 2, 1988.

This invention relates to the marking of products to establish their identity and source.

A major problem experienced in many areas of the world and in connection with many different products is that of product counterfeiting.

Throughout the world, traders provide the products they sell with a visually distinctive appearance, packaging or labels in order that customers can distinguish their products from those of others. As a result, their customers learn to associate the visually distinctive appearance with certain standards of quality, and, if they are satisfied with those standards, will buy products provided with that visually distinctive appearance in preference to others.

Once customers have acquired a preference for products provided with a particular visually distinctive appearance, the traders become vulnerable to product counterfeiting.

A counterfeit product consists of a product that is provided with a visually distinctive appearance confusingly similar to that of a genuine product. Customers seeing the visually distinctive appearance provided to the counterfeit product buy this product in the expectation that they are buying a genuine product.

There are many ways known of providing products with a visually distinctive appearance. In general, the visually distinctive appearance is provided either directly to the product or to an article with which the material is associated, for example a label, wrapper or container. The visually distinctive appearance may be, for example, a distinctive shape or configuration, a distinctive marking, or a combination of the two. A particularly preferred visually distinctive appearance is a trademark.

The material of a counterfeit product may be the same as, or different from the material of a genuine product. Often the material of the counterfeit product is the same, but of inferior quality. For instance, it is usually difficult to distinguish a chemical product having a particular chemical formula and made by one manufacturer, from the same chemical, with the same formula, but made by a different manufacturer. This is particularly so if the two manufacturers use the same production process. For this reason, it is not difficult for the unscrupulous to establish the chemical formula of an active ingredient in a composition, and the relative amounts of the various ingredients in the composition, and then pass off his own product as that of another manufacturer.

In addition to product counterfeiting, product adulteration is another major problem. Product adulteration takes place when a product is tampered with such as by dilution. An example of such a problem lies in the adulteration of lubricating oils, or other oil based products, by addition of a counterfeiter's oil to a genuine product. Such adulteration is not only financially damaging to the oil manufacturer but the consequent lowering of performance which can occur can cause damage to the consumer and consequently harm the reputation of the genuine product.

A method of overcoming this problem has been previously proposed involving the incorporation of dye in the product. Such a strategy is easily copied. However if a marker is incorporated Which is not readily detectable by visual means, samples of product which may have been adulterated may need to be returned to a base laboratory for physical analysis, for example by chromatographic techniques, before one can determine the extent, if any, of adulteration. The consequent delay is inconvenient for, for example, a distributor in an area where there are no readily available back-up laboratory facilities, and lowers the effectiveness of the technique in deterring counterfeiters.

There is clearly a need for a method which can be used in the field for detecting attempts at product counterfeiting, and product adulteration.

WO 87/06383 discloses a method of labelling an item or substrate by means of macromolecules, and, in particular, nucleic acids or proteinaceous markers. According to that document the marker substance is, in general, included on a tag, attached to the item to be marked and the tests described in the document determine the presence or absence of the marker without any quantification of the marker.

European patent application publication number EP-A-0260829 discloses monoclonal and polyclonal antibodies which may be used to identify chlorinated phenols, particularly pentachlorophenol, in materials and to determine the concentration of the chemical in those materials. It is noted in the introduction to the specification that pentachlorophenol is added to materials as a pesticide or a preservative. However, EP-A-0260829 does not disclose the identification of chlorinated phenols in products, that is to say materials provided with a visually distinctive appearance. Furthermore, EP-A-0260829 does not disclose the use of chlorinated phenols as marker compounds. In particular, EP-A-0260829 does not disclose associating a chlorinated phenol with a genuine product for the purpose of distinguishing it from a counterfeit product.

In a poster presentation given by M. J. Wraith et al., at the 6th International Congress of Pesticide Chemistry, Aug. 10–15th, 1986 in Ottawa, Canada, entitled "Development of Immunoassay Methods for Pyrethroid Insecticides", there were disclosed protein conjugates of m-phenoxybenzoic acid and dichlorovinyl cyclopropane carboxylic acid, and polyclonal antibodies prepared using these protein conjugates. Also disclosed was the analysis of the cypermethrin metabolites, m-phenoxybenzoic acid and dichlorovinyl cyclopropane carboxylic acid in black tea, water and soil. However, no disclosure was made of the use of either m-phenoxybenzoic acid or dichlorovinyl cyclopropane carboxylic acid as a marker compound, nor of the detection by immunoassay of either compound in any material provided with a visually distinctive appearance.

SUMMARY OF THE INVENTION

In general, the invention features a method of marking a product for identification in which a low molecular weight hapten is associated with the product as a marker, where the hapten is non-deleterious to the product, inert with respect to the product, and not already associated with the product. A low molecular weight hapten is, for purposes of this application, a molecule which is too small to elicit a significant antibody response when used as an immunogen unless it is coupled with a larger molecule such as keyhole limpet haemocyanin or albumin, but which will elicit such a response when so coupled. Generally, haptens have molecular weights under 1,000 and thus exclude proteins and DNA molecules.

The invention provides a method of labeling a product in such a way that the presence of the marker substance may be easily established by someone who knows the identity of the marker, but could not be routinely determined by a counterfeiter or other person unfamiliar with the marker. Thus, a counterfeit and a genuine product could be distinguished by the absence of the marker in the former and the presence of the marker in the latter.

The invention is also useful for providing a method of indicating other information about the product, such as its date of production, its batch, and consequently, the end of its shelf-life.

The invention also provides a method of marking which allows monitoring of manufacturing or other processes, including such things as process streams and blending controls.

The method of marking provides a way of detecting and monitoring spillages of marked materials.

The method of the invention also provides a means of detecting residues of marked products, such as pesticides, herbicides, fertilizers and other chemicals. The method of the invention also provides a means of detecting marked products which may be organic pollutants, such as TBT and dioxins.

The invention also provides a means of marking products to allow for monitoring of the products for different purposes, such as marking the source country of products for customs, marking toxic wastes, and marking regulated substances.

The invention also provides a method of labeling a product in such a way that the concentration of the marker substance may be easily established by someone who knows the identify of the marker, in order to determine whether the product had been adulterated by way of dilution, concentration changes or the addition of foreign substances.

Other features and advantages of the invention will be apparent from the following description of the preferred embodiments thereof, and from the claims.

DESCRIPTION OF THE PREFERRED EMBODIMENTS

Figure 1:
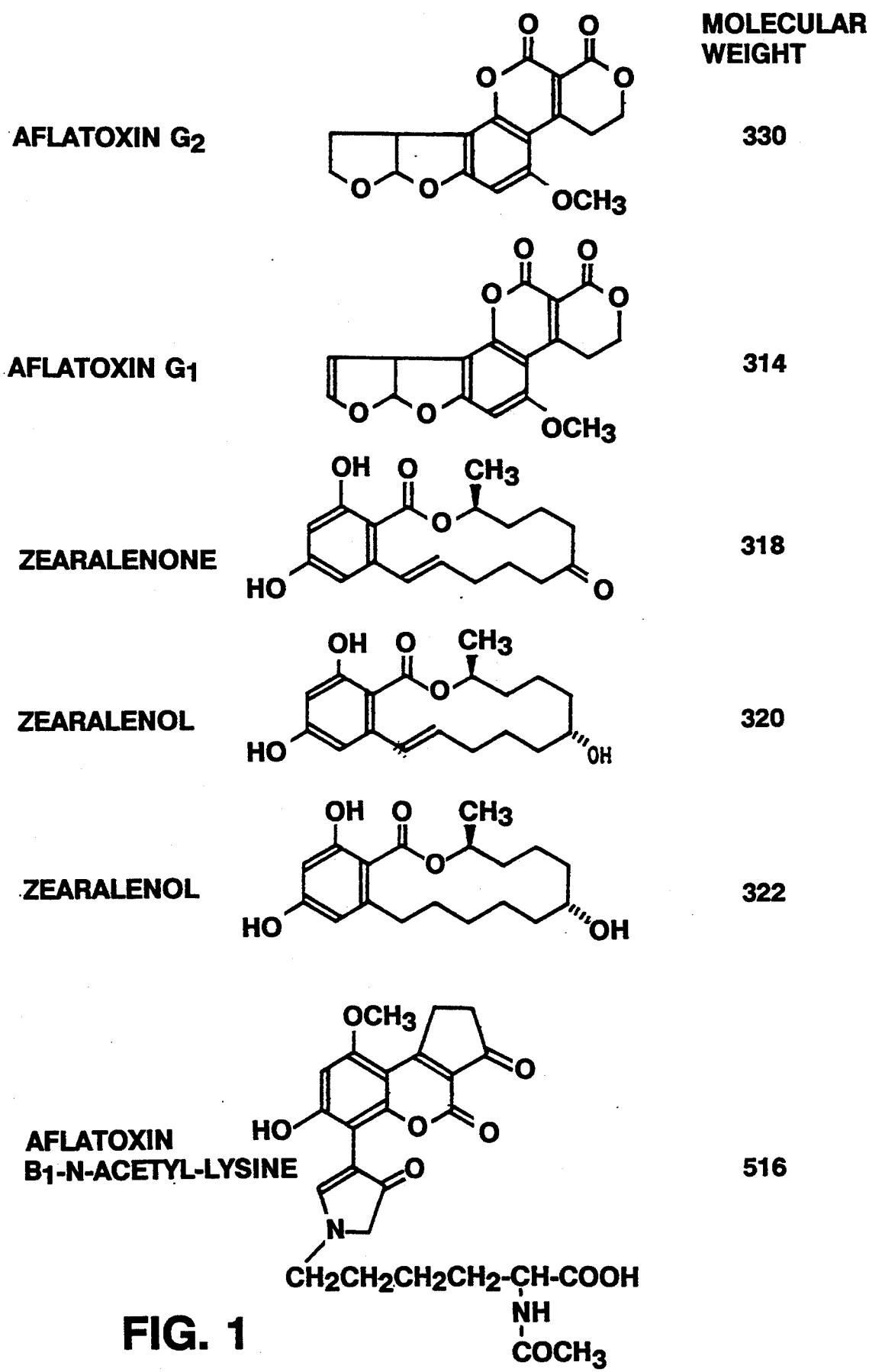
FIG. 1 is a schematic drawing of the formulae of fungal metabolites which can be employed as markers.
Figure 2:
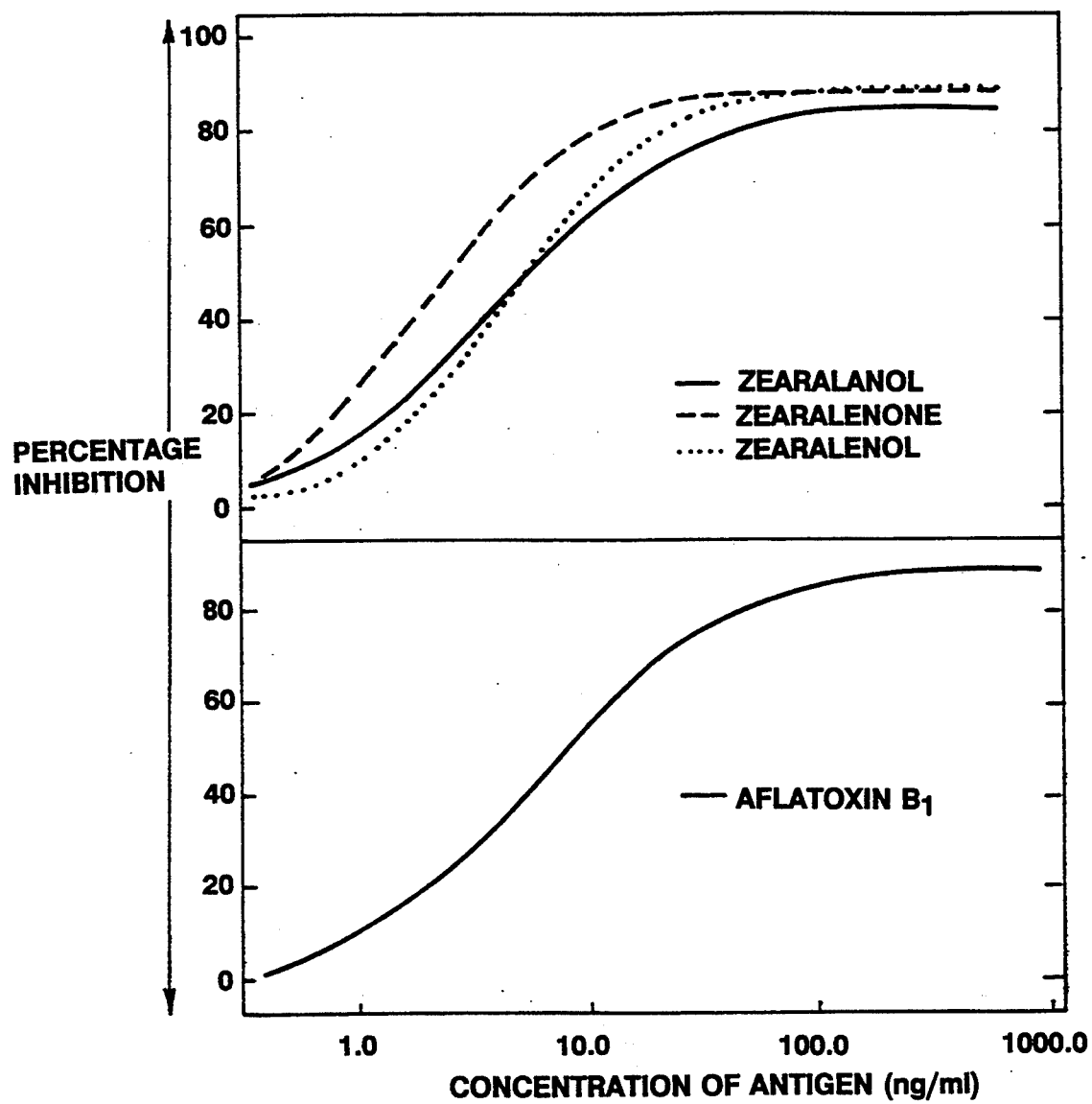
FIG. 2 depicts inhibition ELISA data for anti-RAL monoclonal antibody and anti-aflatoxin antibody.

The low molecular weight hapten marker of the invention is capable of being detected by immunoassay. It should be compatible, i.e., non-deleterious, with the product which it marks. Preferably it will be non-toxic if used in a manner in which it is intended to be ingested. It is preferably visually undetectable.

The marker hapten should in general be one which is not normally present in the chemical or composition; for example, it is not a by-product of the production process, normal impurity, or standard additive for that chemical, or chemical composition. In preferred embodiments, the marker compound is present in very low concentrations, e.g., in the order of micrograms per kilogram of the labelled composition or below. Although it is inert in the sense that it does not react with the product which it labels, it must nevertheless be capable of binding to a complementary binding member, i.e. and antibody, preferably a monoclonal antibody.

It will be appreciated that the marker compound may be associated with the product in a wide variety of ways. Thus the marker compound may be present in or on all or part of the product, or in or on all or part of a label, wrapper or container associated with the product. The marker compound is usually mixed with the product, but may alteratively be present independently of the product, for example the marker may be present in the product packaging or labelling.

The product marked may be solid or fluid.

Examples of solid products include pharmaceutical tablets, capsules and powders; solid formulations of agrochemicals such as insecticides, herbicides, fungicides and fertilizers; textiles such as clothing; recordings such as gramophone records, tape cassettes, floppy discs and compact discs; electrical goods such as television sets, computers and radios; motor vehicle components and cameras; paper such as documents, confidential papers, notes, securities, labels, and packaging; chemical products such as inks, biocides, and rubbers; cosmetics such as creams; and food products.

Examples of fluid products include oil-based products such as lubricating oils, gasoline, diesel and liquified petroleum products; paints; perfumes; cosmetics; drinks such as wine, whisky, sherry, gin and vodka; liquid pharmaceutical formulations such as syrups, emulsions and suspensions; liquid agrochemical formulations; and industrial solvents. The product is preferably liquid, preferably an oil based product such as a lubricating oil.

When the product is an oil-based product such as a lubricating oil, the compound used as a marker compound preferably has a log P in the range of from $-2.5$ to $+5.0$, preferably from $-1.5$ to $4.5$, most preferably from 0 to 4.0. (Log P as used herein means the logarithm of the partition coefficient of a compound between octanol and water at 25° C.). Thus, m-phenoxybenzoic acid, for example, has a log P of 3.9.

It is possible to produce antibodies which are selective for a particular optically active form of a compound. Since it is difficult to distinguish between optically active forms of compounds by conventional analytical techniques, particularly when only trace quantities of the compound are available for analysis, the use of optically active marker compounds may be particularly advantageous.

A hapten suitable for use as a marker compound has been found to be m-phenoxybenzoic acid. Other preferred compounds for marking are erythrosine, 4-aminonaphthalene-1-sulphonic acid, amaranth, dafcol brown, 4-amino-1,1-azobenzene-3,4'-disulphonic acid, mordant yellow 7,4-hydroxy-3-methoxycinnamic acid, 4-hydroxy-3-methoxyphenyl-3-buten-2-one vanillin, ethyl-4-hydroxy-3-methoxycinnamic acid, 7-amino-4-methylcoumarin, chromotrope FB, ponceau 4R, ponceau S, bieberich scarlet, tropaelin O curcumin, coniferyl alcohol, hexyl vanillate, acetovanillone. A list of these marker compounds is set forth below in Table 1.

TABLE 1

MARKER CHEMICALS TO WHICH ANTIBODIES PAIRS HAVE BEEN GENERATED

| | |
|---|---|
| Erythrosine | Chromotrope FB |
| 4-Aminonaphthalene-1-sulphonic acid | Ponceau 4R |
| Amaranth | Ponceau S |
| Dofcol Brown | 4'-disulphonic acid |
| 4-Amino-1, 1-azobenzene-3, 4'-disulphonic acid | Tropaelin O |
| Mordant yellow 7 | Curcumin |
| 4-Hydroxy-3-methoxycinnamic acid | Coniferyl alcohol |
| 4-Hydroxy-3-methoxyphenyl-3-buten-2-one | Hexyl vanillate |
| Vanillin | Acetovanillone |
| Ethyl-4-hydroxy-3-methoxycinnamic acid | |
| 7-Amino-4-methylcoumarin | |

It will be appreciated that a wide range of compounds are suitable as marker compounds so long as they are compatible with and non-deleterious to the product being marked. Thus the use of oil-compatible, water-compatible and solids—compatible compounds as marker compounds is envisaged dependent on the product being marked.

When the product is a liquid, the marker compound is preferably colorless and soluble in the liquid product so that its presence can only be detected by subsequent assay. It is preferably also odorless.

Preferably only trace quantities of marker are used. Typically a marker compound will be incorporated with a product at a concentration in the range of from 1 part per billion (ppb) to 25 parts per million (ppm). Preferably the concentration will be in the range of from 100 ppb to 15 ppm, more preferably 1ppm to 10 ppm. Thus, for example, the concentration of marker compound may be up to about 10 ppm, and dependent on the marker compound, even a few ppb may be sufficient for detection.

The ability to detect concentrations of marker compound at 25 ppm or below is a particular advantage of the method according to the invention. Thus only small quantities of marker compound need to be used.

According to another aspect, the invention provides an oil-based product comprising from 1 ppb to 25 ppm of a visually undetectable, substantially water-soluble marker compound having a log P in the range of from −2.5 to 5.0.

If the marker compound is incorporated with the product in an aqueous medium, the immunoassay may be carried out directly on a sample thereof, if necessary after filtration to remove solids. Otherwise the marker compound must be brought into aqueous solution.

In general, providing a sample of marker compound in aqueous solution will comprise one or more steps selected from solvent extraction of the marker compound from the product; dilution of the product with an aqueous solvent; filtration; evaporation; and solid phase extraction of the marker compound, e.g. purification of the marker compound using an ion exchange resin or chromatography, for example using silica. In the case of a marked oil-based product solvent extraction appears to be necessary.

The solvent chosen for extracting the marker compound from the product prior to assay naturally depends on the natures of the product and the marker. Depending upon the natures of the product and the marker, the solvent will in general comprise one or more of water; hydrocarbons, for example benzene, toluene, xylene, hexane, heptane and octane; sulphoxides, for example dimethylsulphoxide; halogenated hydrocarbons; for example chlorobenzene, methylene chloride, chloroform and carbon tetrachloride; ethers, for example diethyl ether, dioxan and tetrahydrofuran; amides, for example dimethylformamide and dimethylacetamide; nitriles, for example acetonitrile; alcohols, for example methanol, ethanol and propanol; esters, for example ethyl acetate; and ketones, for example acetone. Preferably the solvent comprises water and/or a water miscible organic solvent. When testing lubricating oils marked with m-phenoxybenzoic acid, a suitable extracting solvent is a mixture of a diluent for the oil such as hexane, a water-miscible organic solvent such as acetonitrile, and water. Optionally the extraction solvent may also comprise buffer salts such as Tris buffer (Tris[hydroxymethyl]amino-methane). The solvent system used preferably yields the extracted marker compound in an aqueous phase suitable directly for the subsequent immunoassay.

The present invention facilitates the identification of several different batches of a chemical or chemical composition by the use of a single marker compound. This is because a single marker compound may be employed in different concentrations in different batches and each batch identified by determination of the concentration of the marker in that batch.

In certain preferred embodiments a plurality of marker haptens are included in a chemical or composition. In this case the number of possible permutations of concentration and markers is increased and batches may be identified with increased certainty by measuring relative concentrations of the markers.

In some embodiments of the present invention the marker hapten is extracted from the product into a solvent before binding to its complementary binding member. The solvent is preferably one which is compatible with the complementary binding member. Alternatively, where the extraction solvent is incompatible with the complementary binding member the extract may be diluted with a compatible solvent before binding to the complementary binding member.

The complementary binding member is preferably an antibody and particularly preferably a monoclonal antibody.

The complementary binding member or members are desirably provided on an immunoaffinity column.

The or each marker compound is preferably added at a level of not more than 5 parts per million, and more preferably at not more than 100 parts per billion (by weight).

The hapten markers are molecules to which antibodies may be generated by administering them in association with a carrier molecule.

Such antibodies are raised by known techniques which allow one to obtain monoclonal or polyclonal antibodies specific to a particular hapten.

Antibodies are proteins produced in animals by antibody-producing cells known as B-lymphocytes in response to the exposure of the animal to foreign compounds (antigens). These antibodies bind specifically to the particular compound which stimulate their production.

Antibody-producing cells arise in the spleen of an animal when the animal has been immunized with an immunogenic compound. Not all compounds are immunogenic. In general, compounds with a molecular weight of below 2,000 are not immunogenic. However, antibodies which are specific for such compounds (known as haptens) may be obtained by chemically binding the hapten to a larger immunogenic carrier such as a carbohydrate or protein, and immunizing an animal with the resultant immunogenic conjugate.

The attachment of hapten to immunogenic carrier may be achieved using a bifunctional molecule in a two-stage chemical reaction. This provides a spacer arm between the hapten and carrier which may improve the immune response. In order for the compound to be chemically linked to the carrier or bifunctional molecule, it should itself contain a functional group. Preferred functional groups are amino groups, hydroxyl groups and carboxyl groups.

When an animal has been immunized with an immunogenic substance, a wide variety of different antibody-producing cells are stimulated. The antibodies produced by such a response are known as polyclonal antibodies.

Polyclonal antibodies raised against a particular compound do not all bind with the same specificity to that compound. However, it is possible to obtain antibodies which all bind with the same specificity and affinity to a compound. These antibodies are known as monoclonal antibodies.

In order to obtain such monoclonal antibodies, antibody-producing cells are firstly extracted from the spleen of an immunized animal. These cells are then fused with myeloma cells to produce hybridomas. Fusion may be achieved, for example, by treatment with polyethylene glycol. The hybridomas are capable of producing antibodies, like the precursor antibody-producing cells, but are immortal; they are capable of continuous growth in Vitro. A number of myeloma cells suitable for fusing with antibody producing cells are known and readily available to those skilled in the art. An example of a suitable myeloma cell which is readily available is PX3-63-AG8-653. This cell is available, for example, from the American Type Culture Collection, Rockville, Md., USA under the number ATCC CRL 1580.

Once the antibody-producing cells and the myeloma cells have been fused, the resultant hybridoma cells are separated from the infused cells and cloned by repeated limiting dilution. Cloned hybridomas are then tested to determine which are producing the desired antibodies. This testing may be achieved, for example, by competitive enzyme linked immunosorbent assay (ELISA). Specificity and affinity for a compound may be assessed by the addition of free compound to the ELISA test system to evaluate the ability of the free compound to inhibit binding of the monoclonal antibody to compound which is bound to a solid phase.

Once a particular hybridoma has been selected, monoclonal antibodies may readily be produced in large quantities using well known techniques. If desired, these antibodies may be labelled with an enzyme; e.g. horse radish peroxidase or alkaline phosphatase.

Techniques for producing polyclonal and monoclonal antibodies for a compound are well known to those skilled in the art. Examples of references in which such techniques are described include Methods of Enzymology Volume 70 and Volume 73 Immunochemical Techniques parts A and B respectively Edited by Van Vunakis, H and Langone, J. L., Published by Academic Press 1980 (Part A) and 1981 (Part B), and Kohler, G. and Milstein, C, Nature, Vol. 265, p. 495 (1975).

Referring again to the marker haptens, they may be detected in the sample qualitatively or quantitatively. When the hapten is detected quantitatively, adulteration may be ascertained.

Preferably several markers are included in a chemical or chemical composition products. The ratios of the concentrations of the markers in each chemical or composition labelled are then preferably unit ratios, e.g. in the case where there are two markers the ratio of concentration of one to that of the other may be 1:1, 1:2, 1:3 1:4, etc.

Preferably, where a plurality of markers are present these possess a common site which enables them to bind to, and be concentrated on the same complementary binding member, while they remain separable by subsequent analytical techniques. Thus in some embodiments at least one of the marker compounds may carry an amino acid, nucleic acid, oligonucleotide or oligopeptide substituent which does not affect the binding of the marker compound to its complementary binding member. Such substituents make marker compounds more easily distinguishable from each other by analytical techniques such a HPLC.

Assay of the marker hapten by contact with the antibody is preferably accomplished by competitive enzyme-linked immunosorbent assay (ELISA), although other immunoassay methods may be employed, including enzyme-mediated immunoassay and sandwich immunometric assays. Actual detection of the result of the assay may be by colorimetric means or by alternative detection means such as chemiluminescence or fluorescence.

It will be appreciated that such a detection method is well suited to field operation as no complex laboratory equipment is required.

In a further aspect of the invention, a kit is provided for labelling a chemical or chemical composition and/or for identifying the source of a labelled chemical or composition by the above method, said kit comprising at least one inert marker hapten and respective complementary binding member or members. Preferably the complementary binding member binds the hapten to form an immunological binding pair.

Thus, according to a further aspect of this invention we provide an assay kit for detecting the presence of a visually undetectable, marker hapten associated with a product, comprising means for providing a sample of said marker in a liquid medium, immunoassay means including antibodies specific for the marker compound, detection means for monitoring the immunoassay and means for comparing the result of the immunoassay with the result expected from a genuine product.

A means for providing a sample of said marker in liquid medium may comprise any solvent necessary for bringing the marker into solution and/or filtration means to remove unwanted solids and/or solid phase extraction columns (for example columns containing an ion exchange resin or a chromatography medium such as silica).

An immunoassay means may comprise monoclonal or polyclonal antibodies, supplied in an appropriate quantity.

A detection means for monitoring the result of the immunoassay may be, for example, means to produce and/or measure a colour reaction. Thus a detection means may comprise an enzyme and a substrate for the enzyme. The enzyme may be attached to the hapten, the anti-hapten antibody, or a second antibody directed against the anti-hapten antibody. Examples of enzymes include horse radish peroxidase and alkaline phosphatase. Examples of substrates include o-phenylenediamine dihydrochloride; Amerlite Signal Reagent (available from Amersham International PLC); and p-nitrophenol phosphate. It will be appreciated that an external detection device such as a spectrophotometer, liminometer or fluorimeter may be employed. In this way not only the existence of the marker compound but also the amount present can be determined, thus giving an indication of the extent of adulteration of the product.

A means for comparing the result of the immunoassay with that expected from a genuine product may comprise instructions describing the result expected of a genuine product (comprising, for example, a colour chart, calibration table or calibration curve), or it may comprise a sample of marked material identical to marked genuine product (to be analyzed alongside the unknown sample).

The kit is preferably provided with a representation of the visually distinctive appearance provided to the material of the genuine product. For example the kit may be provided with a representation of a trademark with which the material of the genuine product is provided.

The ability to provide assay means in kit form ensures that a man in the field, such as a distributor of a product in an environment distant from the product source can quickly check the authenticity of the product without recourse to laboratory facilities.

It will be apparent that, since the marker compound is in such low concentrations in the labelled chemical or composition its presence therein is not immediately apparent to someone who is unaware of the addition. Furthermore, it would not be easy for a third party to identify the marker using routine techniques and include it in a counterfeit composition. That is because isolation and concentration of the marker relies on the use of an antibody specific for it and this would not be available to anyone who was ignorant of the identity of the marker.

The invention will now be further described with reference to the following examples.

EXAMPLE 1

Preparation of Protein conjugates of Compound Intended For Use as a Marker Compound A series of protein conjugates of m-phenoxybenzoic acid (a hapten, referred to hereinafter as 'PBA') were prepared by firstly preparing a suitable reactive derivative from PBA by chemical synthesis followed by conjugation of the derivative with the protein. The derivatives were prepared with a $^{14}C$ radiolabel to allow monitoring of the subsequent protein conjugate to check for removal of reagents and to calculate the loading of the protein with the hapten.

i) Preparation of PBA derivatives m-Phenoxybenzoic acid was reacted with thionyl chloride in benzene to give the corresponding benzoyl chloride which was subsequently reacted with 4-aminobutyric acid in the presence of sodium hydroxide followed by acid hydrolysis to give a derivative a) of formula I

where R is $-(CH_2)_3COOH$.

Two further derivatives were prepared by reacting the intermediate benzoyl chloride with b) glycine and c) glycyl glycine in the presence of sodium hydroxide followed by acid hydrolysis to give b) a derivative of formula I where R is $-CH_2COOH$ and c) a derivative of formula I where R is $-CH_2CONHCH_2COOH$.

The derivative a) of formula I was also prepared by reacting benzyl 4-aminobutyrate and 3-(3'- dimethylaminopropyl)-1-ethyl carbodiimide in aqueous tetrahydrofuran to give a compound of formula I where R is $-(CH_2)_3COOCH_2Ph$ followed by hydrogenolysis with a palladium on charcoal catalyst in tetrahydrofuran to yield derivative a).

The derivatives were converted to their sodium salts (which dissolved readily in water) by addition of stoichiometric amounts of sodium bicarbonate or carbonate in water and tetrahydrofuran added until a homogenous solution was obtained followed by evaporation to dryness.

ii) preparation of Protein Conjugates

The derivatives prepared as described in i) above, in the form of their sodium salts, were each dissolved in water, adjusted to pH 8 and cooled to 0° C. A solution, also cooled to 0° C. of 3-(3'-dimethylaminopropyl)-1-ethyl carbodiimide was added to the derivative sodium salt and allowed to stand for 2 minutes to complete formation of the isourea carboxylate.

Each of the derivatives was then bonded to one of the following proteins dissolved in distilled, deionized water and filtered:

bovine serum albumin (M.W. about 68,000)
Chicken gamma globulin (M.W. 125,000 to 750,000)
keyhole limpet hemocyanin (M.W. 3,000,000 to 7,000,000)

The loading was carried out by adding the solution over one minute to the protein with stirring and the mixture kept at 5° C. for several hours to complete the bonding. pH was adjusted to pH 8 as necessary. The loaded protein was dialyzed with saline phosphate buffer pH 7.3 for from 5 to 7 days with daily changing of dialysate and the loading determined by $^{14}C$ radioactivity measurement.

EXAMPLE 2

Production of Monoclonal Antibodies

A conjugate of PBA and bovine serum albumin, 15 moles PBA per mole of protein, was used to produce the antibodies. The PBA-bovine serum albumin was prepared using derivative a) of Example 1 i) in the procedure of Example 1 ii).

Six mice (Balb/c, female) were immunized subcutaneously with a 1:1 emulsion of complete Freund's adjuvant and PBA conjugate (0.1 ml, 50 μg). Each animal received a further 3 injections at 3 weekly intervals but with incomplete adjuvant. Under a similar regimen, a further six animals received a higher dose of conjugate (200 μg). Serum samples from the twelve animals were tested for specific binding to PBA by means of an enzyme-linked immunosorbent assay (ELISA).

The spleen was removed from the animal producing the highest serum concentration of antibodies and the splenocytes used in a fusion with PX3-63-AG8-653 myeloma cells (available from the American Type Culture Collection, Rockville, Md. USA, under the number ATCC CRL 1580). Hybridoma cells were distributed into ten 96-well microtitre plates. Following cell growth, supernatant tissue culture fluids were tested by ELISA for antibody production. Specificity was assessed by the addition of free PBA to the test system to determine the inhibition of binding of the antibodies to the solid phase PBA target in the ELISA method. Cells from several positive wells were grown to produce cell stocks and then cloned by the limiting dilution technique. Following further cell growth the resulting supernatants were tested as above and the contents of several positive wells grown-up and cloned again. The cells in wells identified as positive, following the second cloning, were grown-up to produce supernatants containing sufficient monoclonal antibodies for preliminary assay development.

In order to generate sufficient monoclonal antibodies for medium-term requirements, 5 clonal cell hybridomas were chosen for the production of antibody-rich ascites fluid. Ten, pristine-primed, female Balb/c mice per hybridoma, were each inoculated intraperitoneally with up to $10^7$ hybridoma cells. Ascites fluids were harvested, pooled and stored deep frozen.

Antibodies were also prepared by growing hybridoma cells in vitro in stirred tissue culture vessels.

A sample of one of the clonal cell hybridomas has been deposited with the European Collection of Animal Cell Cultures (ECACC), PHLS Centre for Applied Microbiology and Research, Porton Down, Salisbury SP4 0JG, United Kingdom, with effect from 10th Jan., 1989 under accession number 89011001.

EXAMPLE 3

Assay of a Marked Lubricating Oil

A marked lubricating oil (available under the Shell Trade Mark Rimula X) was prepared containing 10 ppm of m-phenoxybenzoic acid. A series of 2ml samples was prepared containing varying percentages of marked oil and unadulterated oil.

PBA was extracted for assay from each oil sample by the following method.

Extraction of PBA from Oil

1. The oil sample on which the authenticity check was to be carried out was placed in a sealable vessel. Five volumes of hexane and 1 volume of 20% acetonitrile in 0.05M Tris/HCl pH 7.5 were then added to the oil and the vessel sealed. The mixture was then shaken for one minute and the resulting suspension allowed to separate. This took approximately 30 seconds.

2. An aliquot was taken from the lower phase of the separated mixture using a disposable plastics pipette and applied to a 3 ml NH2 Bond Elut column (an ion exchange resin column obtained from Jones Chromatography). The sample of extract was passed through the column by the application of pressure and the column then washed with 4×1 ml aliquots of distilled water.

3. The column was then eluted with 2 ml of a solution of 0.05% (v/v) Tween 20 in saline. This solution removed any bound PBA. Each recovered PBA solution was then subjected to competitive enzyme linked immunosorbent assay (ELISA) by the following method.

Immunoassay Method (with detection by colorimetric means)

1. A plastic well/tube was coated with a fixed level of a PBA-chicken gamma globulin conjugate prepared as described in Example 1. To achieve this coating, a measured aliquot of 100 μl conjugate, at a concentration of 10 μg/ml was placed in the well/tube. This was then incubated at a carefully controlled temperature for a fixed time and a reproducible level of coating was achieved by adsorption. After the coating period, the wells were washed and could be stored at 4° C.

2. The PBA-containing solution to be assayed was placed in a pre-coated well in the presence of a limiting level of specific monoclonal antibody prepared as described in Example 2. The sample of antibody was used at a dilution of 1:1000. The basis of the assay is the competition for binding of this antibody between the PBA in solution and PBA which is immobilized on the surface of the well as conjugate. After a fixed period of time the solution in the well was removed and the well washed. The antibody remaining in the well after washing is that which bound to the immobilized PBA, the level of antibody remaining is thus inversely proportional to the level of PBA which was previously present in free solution.

3. A solution of second antibody-enzyme conjugate was added to the well. The second antibody enzyme conjugate used was IgG (alkaline phosphatase linked to rabbit anti-mouse immunoglobulin G—available from ICN Biologicals) at 1:1000 dilution, 100 μl per well. This conjugate binds to any of the primary antibody which has remained, bound to the immobilized conjugate in the well. The second antibody-enzyme conjugate was added in excess and, again, unbound material was removed by washing. After washing, the level of second-antibody-enzyme conjugate remaining in the well is directly proportional to the level of primary antibody bound in step 2 described above.

4. A solution containing a substrate for the enzyme of the second antibody-enzyme conjugate was added to the well and the level of enzyme present was determined by measuring the formation of coloured product. The substrate was p-nitrophenyl phosphate disodium salt (available from Sigma Chemical Co. as Sigma 104 phosphatase substrate) at a concentration of 1 mg/ml in 10% diethanolamine buffer pH 9.8. The formation of yellow coloured product was measured at 405 nm using a vertical beam visible light absorption spectrophotometer (MR610 Microplate reader—Dynatech).

Two sets of results of the colorimetric assay of the oil samples containing varying percentages of marked oil are given in Table 2 below. The results are expressed as a percentage of marked oil in the sample.

TABLE 2

| Sample No. | 1 | 2 | 3 | 4 | 5 | 6 | 7 | 8 | 9 | 10 |
|---|---|---|---|---|---|---|---|---|---|---|
| Calculated | 75 | 25 | 100 | 0 | 50 | 0 | 33 | 100 | 10 | 50 |
| Observed Set A | 47 | 14 | 100 | 0 | 50 | 0 | 29 | 100 | 0 | 42 |
| Observed Set B | 76 | 33 | 93 | 0 | 55 | 0 | 22 | 118 | 31 | 55 |

EXAMPLE 4

Assembly of an Assay Kit and its use in an Assay of a Marked Lubricating Oil

An assay kit, suitable for testing up to three possible counterfeit samples of lubricating oil, was assembled. The kit comprised:
(1) 5 plastic tubes coated with a PBA-chicken gamma globulin conjugate (prepared as described below);
(2) 5 ion exchange resin columns, (3 ml NH2 Bond Elut columns, obtained from Jones Chromatography);
(3) 5 10 ml volumes of extracting solvent, consisting of 8 ml hexane and 2 ml of 40% acetonitrile in 0.05M Tris/HCl, pH 7.5;
(4) 1 sample of lubricating oil containing 10 ppm of m-phenoxybenzoic acid (representing a sample of a marked genuine product);
(5) 1 sample of lubricating oil containing no m-phenoxybenzoic acid;
(6) 5 2 ml volumes of PBA-Specific monoclonal antibody diluted ten-fold in phosphate buffered saline (PBS, available in tablet form from Oxoid) containing 0.05% w/v Tween 20 (polyoxyethylene-sorbitan monolaurate, available from Sigma Chemical Company, Catalogue Number P1379);
(7) 1 volume of antibody-enzyme conjugate (comprising horse radish peroxidase conjugated rabbit immunoglobulins to mouse immunoglobulins, available from DAKO Limited, Catalogue Number P161);
(8) Chemiluminescent substrate (Amerlite Signal Reagent, available from Amersham International PLC, Catalogue Number LAN 4400);
(9) Wash solution, consisting of 0.05% (v/v) Tween 20 in saline (ST);
(10) Column wash, consisting of distilled water; and
(11) 1 instruction sheet.

Preparation of plastic tubes coated with a PBA-chicken gamma globulin conjugate

Plastic tubes were coated with a fixed level of a PBA-chicken gamma globulin conjugate prepared as described in Example 1. To achieve this coating, a measured aliquot of 500 µl conjugate, at a concentration of 20 µg/ml was placed in the tube. This was then incubated for 3 hours at room temperature and a reproducible level of coating was achieved by adsorption. After the coating period, the tubes were washed with the saline/Tween solution (ST), described in Example 3, dried and stored desiccated, preferably at 4° C., until required.

Use of Assay Kit to Assay Marked Lubricating Oils

1. In order to carry out the assay, the first step is to prepare the chemiluminescent substrate, following the manufacturer's instructions.

2. The two samples of lubricating oil belonging to the kit and three "unknown" samples of lubricating oil are extracted using the 5 volumes of extracting solvent and 5 ion exchange columns, according to the method of Example 3. The columns are then washed with two 2 ml aliquots of column wash.

3. Each of the columns is then eluted with one 2 ml aliquot of wash solution into small glass bottles containing the 2 ml volumes of PBA-specific monoclonal antibody.

4. The bottle contents are then mixed, and at least 500 µl from each of the 5 mixtures is transferred to the five plastic tubes coated with PBA-chicken gamma globulin conjugate. After 5 minutes the solutions in the tubes are tipped away and the tubes washed once with wash solution.

5. 500 µl of a solution of the antibody-enzyme conjugate is added to each of the tubes. After a 5 minute incubation the contents of the tubes are tipped away and the tubes are washed 5 times with wash solution.

6. The chemiluminescent substrate, 1 ml, is then added to the tube and after 2 minutes the light output measured, following the manufacturers instructions for use of a portable, battery powered, tube liminometer (available from Dynatech Laboratories Ltd.). The readout of the instrument is a 3 digit number in the range 0–999.

7. The reproducibility of the method has been assessed over a series of 35 assays, carried out by two operators, over a four week period. The inter-assay coefficient of variation (CV) for this series of experiments was 9.1%. It was found that if the assay had been performed correctly, the ratio of the positive control (lower reading) to the negative control (higher reading) was 0.612±0.056 (i.e. ±1 Standard Deviation (SD). For an "unknown" oil a value of 0.725 or greater indicated a "possible counterfeit" sample.

EXAMPLE 5

Assay of marked gasoline 13 ml samples of leaded and unleaded gasoline were marked with 3 levels of PBA (10, 5 and 2.5 ppm). They were extracted with Tris buffer (2 ml, 0.05M, pH 7.5). The extracts were assayed as described in Example 3 and PBA quantified using a calibration curve of standards prepared in an unmarked gasoline extract. Corresponding samples were prepared containing radiolabelled PBA enabling extraction efficiencies to be determined and allowing comparison between observed and expected values. The results are shown in Table 3.

TABLE 3

A comparison of observed and expected values for aqueous extracts assayed against a calibration curve in unmarked gasoline extract

| Sample | Blank | 10 ppm Extract | 10 ppm Extract diluted 1:2 | 1:4 | 1:8 | 5 ppm Extract | 5 ppm Extract diluted 1:2 | 1:4 | 2.5 ppm Extract |
|---|---|---|---|---|---|---|---|---|---|
| Leaded gasoline | | | | | | | | | |
| Expected | 0 | 46* | 23 | 11.5 | 5.7 | 23 | 11.4 | 5.7 | 11.4 |

TABLE 3-continued

A comparison of observed and expected values for aqueous extracts assayed against a calibration curve in unmarked gasoline extract

| Sample | Blank | 10 ppm Extract | 10 ppm Extract diluted 1:2 | 1:4 | 1:8 | 5 ppm Extract | 5 ppm Extract diluted 1:2 | 1:4 | 2.5 ppm Extract |
|---|---|---|---|---|---|---|---|---|---|
| (radiochemistry) Observed Unleaded gasoline | 0.9 | 47 | 22.5 | 11.0 | 6.4 | 29 | 13.5 | 5.3 | 13.5 |
| Expected (radiochemistry) | 0 | 33 | 16.2 | 8.1 | 4.1 | 15.5 | 7.7 | 3.9 | 7.5 |
| Observed | 0.9 | 41 | 18.5 | 7.0 | 3.8 | 14.5 | 6.2 | 3.4 | 7.6 |

*All values quoted in ppm.
These results demonstrate the concentration effect achieved by extracting PBA from 13 ml of gasoline into 2 ml of Tris buffer, and convincingly demonstrate that gasoline marked with PBA may be distinguished from unmarked gasoline by immunoassay.

EXAMPLE 6

Assay of marked pharmaceutical

Marked Samples of Paracetamol (acetaminophen—a mild pain killer and anti-pyretic agent) and Naproxen (a non-steroidal anti-inflammatory agent) were prepared containing 20 ppm solid PBA. Portions of each (1 g) were added to 10 ml of PBS/Tween (described in Example 4) in a ml glass bottle. Similarly non-marked assay blanks were prepared for both materials. The bottles were tumbled overnight to extract the PBA into the PBS/Tween. Following separation of undissolved material by centrifugation, sample aliquots (250 μl) of the supernatant solutions were added to 250 μl of PBA specific antibody and analyzed using an assay kit, similar to that described in Example 4.

From the results presented in Table 4 it was demonstrated that the marked pharmaceutical were clearly distinguishable from the non-marked pharmaceutical.

TABLE 4

| Drug | Unmarked* | Marked* | Ratio (%) |
|---|---|---|---|
| Paracetamol | 400 | 288 | 72 |
| | 394 | 275 | 70 |
| | 377 | 283 | 75 |
| | 378 | 278 | 74 |
| | 281 | 206 | 73 |
| | 266 | 203 | 76 |
| | 386 | 303 | 78 |
| | 398 | 267 | 67 |
| | 517 | 357 | 69 |
| | 480 | 378 | 79 |
| | 469 | 379 | 80 |
| | Mean Ratio74 | S.D. = 4.2 | C.V. = 5.7% |
| Naproxen | 517 | 350 | 68 |
| | 503 | 337 | 67 |
| | 355 | 260 | 73 |
| | 313 | 226 | 72 |
| | 279 | 185 | 66 |
| | 269 | 220 | 81 |
| | 269 | 204 | 76 |
| | 245 | 153 | 64 |
| | Mean Ratio = 71 | S.D. = 5.7 | C.V = 8.0% |

*Values indicated were read from the tube liminometer described in Example 4.

EXAMPLE 7

Assay of marked perfume

A sample of 'Eau de Cologne' was prepared containing 20 ppm of PBA. 2 ml of this marked material and 2 ml of the unmarked material were placed in small glass test tubes and evaporated in a gentle air stream to incipient dryness. 2 ml of PBS/Tween (described in Example 4) was added to the oily residue and the tube contents mixed vigorously by vortex mixing. The insoluble, heavier than water, oil was then separated by centrifugation and sample aliquots of the supernatant solution were analyzed as described in Example 6. From the results presented in Table 4 it was demonstrated that the marked perfume was clearly distinguishable from the unmarked equivalent.

TABLE 5

| Perfume | Unmarked* | Marked* | Ratio (%) |
|---|---|---|---|
| Eau de Cologne | 866 | 104 | 12 |
| | 851 | 243 | 29 |
| | 655 | 107 | 16 |
| | 722 | 133 | 18 |
| | 710 | 126 | 18 |
| | 782 | 196 | 25 |
| | Mean Ratio = 20 | S.D. = 6.2 | C.V. = 31.6% |

*Values indicated were read from the tube liminometer described in Example 4.

As an alternative approach marked and unmarked Eau de Cologne were diluted ten-fold with PBS/Tween and assayed directly as outlined in Example 6. The results are presented in Table 6 and show that this alternative method also permits clear distinction between unmarked and marked perfume.

TABLE 6

| Perfume | Unmarked* | Marked* | Ratio (%) |
|---|---|---|---|
| Eau de Cologne | 736 | 499 | 68 |
| | 760 | 522 | 69 |
| | 494 | 324 | 66 |
| | 382 | 267 | 70 |
| | 401 | 233 | 58 |
| | 385 | 257 | 68 |
| | 352 | 210 | 60 |
| | 484 | 307 | 63 |
| | 640 | 426 | 67 |
| | Mean Ratio = 65.4 | S.D. = 4.2 | C.V.-6.4% |

EXAMPLE 8

Assay of marked drink

A sample of blended whisky was prepared containing 20 ppm of PBA. The marked whisky and a corresponding sample of the unmarked whisky were diluted 4-fold with PBS/Tween and sample aliquots (250 μl) were analyzed using the method described in Example 6. The results presented in Table 7 demonstrate that the marked whisky is clearly distinguishable from the unmarked whisky.

TABLE 7

| Drink | Unmarked* | Marked* | Ratio (%) |
|---|---|---|---|
| Whisky | 375 | 119 | 31 |

TABLE 7-continued

| Drink | Unmarked* | Marked* | Ratio (%) |
|---|---|---|---|
| | 396 | 158 | 39 |
| | 381 | 180 | 47 |
| | 449 | 110 | 25 |
| | 435 | 104 | 24 |
| | 427 | 109 | 26 |
| | 431 | 95 | 22 |
| | 421 | 116 | 28 |
| | 387 | 117 | 30 |
| | 440 | 86 | 19 |
| | 412 | 122 | 30 |
| | 386 | 122 | 32 |
| | 353 | 107 | 30 |
| | 474 | 115 | 24 |
| | 452 | 106 | 23 |
| | 446 | 111 | 25 |
| Mean Ratio = 28.4 | S.D. = 6.9 | C.V. = 24% | |

*Values indicated were obtained from the tube liminometer described in Example 4. It was noted in this Example that the signal generated took approximately 20 minutes to develop.

COVERT SURFACE MARKING

In one application of the invention, it is desired to apply the hapten molecule to a surface using an impact or non-impact printing method. The laid down hapten will be subsequently visualized by the application of the other member of the specific binding pair. Since haptens are either not compatible with the ink formulation or do not have good adhesion properties to the surface, it is sometimes necessary to bond the hapten to a polymeric backbone. The hapten-polymer will be soluble in the ink formulation and still be recognized by the specific binding pair member when applied. It should show good adhesive properties to surfaces such as glass, plastic or metal.

In one embodiment of the method, the hapten is chemically linked to a polymer through suitable conjugation chemistry. The subsequent hapten-reacted polymer is dissolved or suspended in an ink formulation capable of being applied through ink jet printing or conventional printing. Once dry, the hapten-polymer can be revealed by application of the specific binding pair linked to a signal compound such as an enzyme, latex bead or fluorescent tag.

The hapten polymer conjugates can be used not only to label surfaces, but can be incorporated into products (either liquids or solids) as well.

Below is given a specific example of hapten-polymer conjugation. 1-Amino-4-naphthalene-sulphonic acid (ANS)(220 mg) and polyacrylic acid (1.4 g) are dissolved in HPLC grade water (25 ml). Dimethylaminopropyl-ethylcarbodiimide (300 mg) is added in 50 mg portions over 1 hour, adjusting the pH to 5.5 (with 1M hydrochloric acid) after each addition. The solution is subsequently stirred overnight at room temperature. Following this, the reaction mixture is dialyzed against HPLC grade water (five times against 5 liters each time) over a period of five days. The resulting dialysate is freeze-dried for storage.

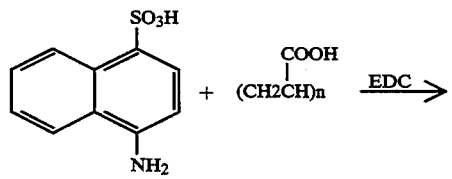

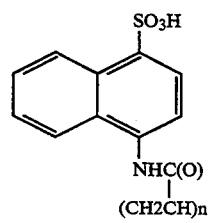

Fungal Metabolites

In the following examples members of two separate groups of fungal metabolites are used as examples of small organic molecules which may be used at very low concentrations to label a substrate and which may be extracted specifically by immunoaffinity chromatography and quantified in order to allow identification of both the source and batch of that substrate. Although the fungal metabolites employed in these examples are toxins the results obtained indicate that the technique could be extended so that pharmaceutical and food additives could be labelled with other small molecules which present no risk to human health.

Two monoclonal antibodies directed against the two separate groups of fungal metabolites are used in the examples. The first, directed against resorcyclic acid lactones (RALS), reacts with the three molecules zearalenone, zearalenol and zearalanol which are readily separated by high performance liquid chromatography (HPLC). The second antibody reacts with several aflatoxins (the other group of fungal metabolites). These aflatoxins may also be separated by HPLC.

Each monoclonal antibody reacts with several similar fungal metabolites because the antigen binding sites on the antibody are directed towards a chemical species which is common between all fungal metabolites of a particular group. It is also possible to derivatize certain parts of the metabolites without hindering their binding to the antibody. For example, N-acetyllysine aflatoxin $B_1$ is still bound by the anti-aflatoxin antibody. The structures of the small organic molecules used in this study are shown in FIG. 1.

It is possible to use amino acids as building blocks to generate an enormous variety of potential marker chemicals with which to mark high added value products. As a model the applicants have therefore conjugated one amino acid derivative, called N-acetyllysine to aflatoxin $B_1$ to exemplify this procedure, and demonstrated the use of this derivative in the marking of a cosmetic product.

MATERIAL AND METHODS

A. Conjugation Reactions

A(i) preparation of N-acetyllsine-aflatoxin $B_1$

Aflatoxin $B_1$ (16.7 mg) was dissolved in dichloromethane (1 ml). Chlorine gas was bubbled through the solution for 5 minutes followed by evaporation under vacuum. The resultant mixture of compounds including 8,9-dihydro-8,9-dichloroaflatoxin $B_1$, was dissolved in 0.6 ml of dimethysulphoxide (DMSO) and mixed with 500 mg of N-acetyllysine dissolved in 20 ml of 0.1M phosphate buffer (pH 7.4). The reagents were mixed for 48 hours at room temperature followed by high performance liquid chromatography (HPLC) purification on an S5-ODS 2 column eluted with an acetonitrile in water gradient as follows:

| Time | % acetonitrile: water (v/v) |
|------|------------------------------|
| 0    | 0                            |
| 6    | 30                           |
| 12   | 100                          |
| 15   | 100                          |
| 17   | 0                            |
| 27   | 0                            |

A(ii) Preparation of Aflatoxin-Protein Conjugates

Briefly, aflatoxin $B_1$-ovalbumin was prepared for inoculation of mice (see below) by direct chlorination of aflatoxin $B_1$ to give 8,9-dihydro-8,9-dichloro-aflatoxin $B_1$, (Sabbioni et al., 1987), followed by reaction with ovalbumin in 0.1M phosphate buffer (pH 7.4) and dialysis. The resultant antigen consisted of 10 to 15 molecules of aflatoxin $B_1$ covalently coupled to ovalbumin.

Aflatoxin $B_1$ was coupled to bovine serum albumin (BSA) in the same way for coating of ELISA plates (see below).

A(iii) preparation of zearalenone-Protein conjugates

Briefly, zeralenone-ovalbumin was prepared for inoculation of mice by carboxylation of hydroxyl groups on zearalenone with carboxymethoxyalanine followed by reaction between the new carboxyl group and amino groups on the protein by carbodiimide reaction (Thouvenot and Morfin, 1983). The resultant antigen consisted of 10 to 15 molecules of zearalenone covalently linked to 1 molecule of ovalbumin.

Zearalenone was also coupled to bovine serum albumin (BSA) in the same way for coating of ELISA plates.

B Preparation of Monoclonal Antibodies

B(i) Inoculation of mice

Antigens (prepared as protein conjugates as described above) were prepared as 1 mg/ml solutions in a 50% (v/v) emulsion of Freund's complete adjuvant in phosphate buffered saline. This emulsion was inoculated into the peritoneal cavity of 10 C57 black×balb c f-1 female mice. Several inoculations (300 ug antigen-/inoculation) were performed at approximately 3-weekly intervals followed by sino-orbital bleeding of the mice. Antiserum levels were monitored by indirect and indirect-inhibition enzyme linked immunosorbent assays (ELISA) for antibodies with specific binding of aflatoxin/zearalenone.

B(ii) Mouse spleen Fusion Technique

HT medium consisted of RPMI medium with L-glutamine (Gibco Europe Ltd.) containing (20% v/v) foetal calf serum, 0.05 mM 2-mercaptoethanol, 1 mM sodium pyruvate, 100 mM hypoxanthine, 100 mM thymidine, 100 ug/ml gentamycin and 2.5 ug/ml fungizone. X63 myeloma cells (Flow Laboratories, UK) were grown in HT medium with the hypoxanthine and thymidine replaced by 8-azaguanine (100 mM). Spleen cells from one immunized mouse spleen ($10^8$) were fused with X63 myeloma cells ($5\times10^6$ in log phase) using GC grade polyethylene glycol 4000 (Merck) 50% w/v inserum-free medium containing 20% (v/v) dimethyl sulphoxide (DMSO) added slowly over 60 seconds, followed by 90 seconds standing at room temperature. The mixture was gradually diluted with 10 ml GKN (8 g NaCl, 0.4 g KCl, 1.42 g$Na_2HPO_4$, 0.78 g $NaH_2PO_4.2H_2O$, 2 g glucose, 0.1 g phenol red in 1L $H_2O$) over 5 minutes, followed by standing at room temperature for 10 minutes. Cells were distributed into 10×96-well Costar tissue culture plates (Northumbria Biologicals, UK), containing approximately $10^4$ mouse peritoneal macrophages per well, and hybridomas selected in HAT medium (HT medium containing aminopterin). After approximately two weeks, supernatants were screened for specific antibody production by enzyme-linked immunosorbent assay (ELISA) and specificity confirmed by inhibition ELISA as described below. Positive hybridomas were cloned by limiting dilution.

B(iii) ELISA Techniques

Solutions and buffers. PBS (11.3 mM KCl, 0.7 mM $KH_2PO_4$, 8.2 mM $Na^2$ $HPO_4$, 8.2 mM $Na_2HPO_4$, 138 mM NaCl, pH 7.2). Solution A: PBS containing 1.5 mM $MgCl_2$, 2 mM 2-mercaptoethanol, 0.05% (v/v) Tween 20. Solution B: 10 mM $K_2HPO_4$, 150 mM NaCl, 1% w/v bovine serum albumin, pH 7.2. Solution C: 3, $3^1$, 5, $5^1$-Tetramethylbenzidine (100 ug/ml) freshly prepared in 100 mM trisodium citrate, 100 mM sodium acetate, (pH 6.0) with $H_2O_2$ (20 ul of 100 volumes per 100 ml of solution).

Techniques Indirect ELISA and inhibition ELISA techniques were used as previously described (Voller et al, 1979) to screen and quantify the monoclonal antibodies. Five modifications were made to these procedures: (i) Either aflatoxin $B_1$-bovine serum albumin, or zearalenone-bovine serum albumin antigens (50 ng/well) in PBS were dried at 37 C. for 24 hours onto clear polyvinyl chloride 96-well Costar microtitre plates (Northumbria Biologicals, UK) during coating; (ii) solution A was used for washing plates (four times) between incubation steps; (iii) first and second antibodies were diluted in solution B and incubated on the plates for 1 hour at room temperature with shaking; (iv) for a competitive inhibition ELISA, mixtures of antigen and antibodies were incubated for 1 hour at room temperature on the plate (total volume of 75 $\mu l$ ) prior to washing and subsequent step; (v) prior to incubation with substrate (solution C) plates were washed six times with solution A and twice with distilled water. fifteen minutes after incubation with substrate the reaction was stopped with an equal volume of 2M $H_2SO_4$.

C preparation of Immunoaffinity Columns

An immunoaffinity resin was prepared by reacting cyanogen bromide Sepharose CL-4B resin (Pharmacia Ltd) with monoclonal antibody (ratio 1 ml resin to 2.5 mg of antibody). Cyanogen bromide Sepharose CL-4B was activated by swelling in 75 ml/g of 1 mM HCl. The resin was then washed with 5 ml/g of coupling buffer (100 mM sodium hydrogen carbonate, 500 mM sodium chloride, pH 8.3). Antibody was diluted to 1.56 mg/ml with PBS followed by diluting with an equal volume of coupling buffer. This mixture was reacted with the swelled, washed resin for 1 hour at room temperature with mixing. The resin was filtered and mixed with ethanolamine (1M at pH 8.0) for 1 hour at room temperature. The resin was washed and stored with PBS containing 0.05% w/v sodium azide at pH 7.4.

Aliquots of the finished resin (0.04 ml settled bed volume) were then supported between porous frits in plastic columns. These columns were examined for their ability to bind mycotoxin standards when these were applied in 50 ml of PBS and eluted with acetonitrile (2 ml). Quantification was by HPLC analysis.

D Extraction Methods

D(i) Extraction of Resorcyclic acid lactones (RALS) from pharmaceutical Products Concentrations of standard RAL solutions were determined from absorbance determinations at lambda max, the extinction coefficient for the particular RAL and its molecular weight. Aliquots of ground paracetamol tablets (6 g per aliquot) were spiked with 2.4 ug of each of the RALS, zearalenone, zearalenol and zearalanol, in different combinations as shown in Table 8 below. Each sample was then extracted by blending with 12 ml of 30% (v/v) acetonitrile: water for 2 minutes. Each sample was centrifuged at 1400 g (av) for 2 minutes and 4 ml was removed and diluted to 40 ml with distilled water prior to immunoaffinity chromatography on columns prepared in section 2.C. The column was washed with 10 ml of distilled water prior to elution with 2 ml of acetonitrile; 2 ml of HPLC grade water was added and the volume measured.

approximately 600 ul. This sample was diluted with HPLC water prior to chromatography through an S5 ODS 2HPLC column using a gradient as described in section A(i) for elution. Peak areas of samples were compared with peak areas of standards of known concentration for quantification of N-acetyl-lysine-aflatoxin $B_1$.

Method B:

N-acetyl-lysine-aflatoxin $B_1$ (500 ng) was spiked into 0.5 ml of Aramis aftershave. The mixture was diluted to 50 ml with anti-aflatoxin immunoaffinity columns bound in excess of 2 ug of aflatoxin $B_1$ from 50 ml of PBS. They consistently bound in excess of 90% of up to

TABLE 8

EXTRACTION OF SMALL ORGANIC MOLECULES PRO PARACETAMOL

| | ZEARALENOL | | | ZEARALANOL | | | ZEARALENONE | | | AFLATOXIN $G_1$ | | | AFLATOXIN $G_2$ | | |
|---|---|---|---|---|---|---|---|---|---|---|---|---|---|---|---|
| | Amount Added ng/g | Amount Recovered ng/g | % Recovery | Amount Added ng/g | Amount Recovered ng/g | % Recovery | Amount Added ng/g | Amount Recovered ng/g | % Recovery | Amount Added ng/g | Amount Recovered ng/g | % Recovery | Amount Added ng/g | Amount Recovered ng/g | % Recovery |
| 1 | 400 | 344 | 86 | 400 | 340 | 85 | 400 | 356 | 89 | 0 | 0 | 0 | 0 | 0 | 0 |
| 2 | 400 | 280 | 70 | 0 | 0 | 0 | 400 | 380 | 95 | 0 | 0 | 0 | 0 | 0 | 0 |
| 3 | 400 | 288 | 72 | 400 | 404 | 101 | 0 | 0 | 0 | 0 | 0 | 0 | 0 | 0 | 0 |
| 4 | 0 | 0 | 0 | 400 | 396 | 99 | 400 | 412 | 103 | 0 | 0 | 0 | 0 | 0 | 0 |
| 5 | 0 | 0 | 0 | 0 | 0 | 0 | 400 | 388 | 97 | 0 | 0 | 0 | 0 | 0 | 0 |
| 6 | 400 | 356 | 89 | 0 | 0 | 0 | 0 | 0 | 0 | 0 | 0 | 0 | 0 | 0 | 0 |
| 7 | 0 | 0 | 0 | 400 | 320 | 80 | 0 | 0 | 0 | 0 | 0 | 0 | 0 | 0 | 0 |
| 8 | 0 | 0 | 0 | 400 | 320 | 80 | 400 | 400 | 0 | 0 | 0 | 0 | 0 | 0 | 0 |
| 9 | 0 | 0 | 0 | 0 | 0 | 0 | 0 | 0 | 0 | 20 | 15.5 | 76.3 | 20 | 16 | 80.0 |

Samples (250 ul) were chromatographed on an S5 ODS 2 HPLC column by socratic elution (50% (v/v) acetonitrile:water) and absorbance was monitored at 236 nm. Standards of comparable peak area were chromatographed before and after repeat sample runs in order to quantify the concentration of RALs occurring in each eluent.

D(ii) Extraction of aflatoxins from pharmaceutical products.

The concentrations of aflatoxin $G_1$ and $G_2$ standards were determined spectrophotometrically and 200 ng of each were used to spike 10 g of ground paracetamol followed by blending for 2 minutes with 20 ml of 30% (v/v) acetonitrile: water. This was then centrifuged at 1400 g (av) for 2 minutes. 4 ml of supernatant was removed and added to 44 ml of PBS, followed by immunoaffinity chromatography as described for RALS. Eluted aflatoxins were chromatographed on an S5 ODS 2 column isocratically eluted with 40% (v/v) of (5.4 v/v) acetonitrile:methanol) in water with post column derivatization of the aflatoxins with saturated aqueous iodine solution prior to fluorescence monitoring. Standards were chromatographed before and after repeat sample runs in order to quantify the concentration of aflatoxins in the eluent.

D(iii) Extraction of Derivatized Lysine from Cosmetics

N-acetyl Lysine-Aflatoxin $B_1$ was dissolved in water at 1 mg/ml by weight, and this stock solution was used to spike Aramis aftershave which was extracted using two methods.

Method A:

N-acetyl-lysine-aflatoxin $B_1$ (2 ug) was spiked into 2 ml of Aramis aftershave. After approximately 30 minutes HPLC water (1 ml) was added and the mixture rotary evaporated to a volume of approximately 1 ml. This was diluted with 50 ml of PBS followed by immunoaffinity chromatography. N-acetyl lysine aflatoxin $B_1$ that bound to the column was eluted with 2:1 (v/v) acetonitrile: water followed by rotary evaporation to 1000 ng of either aflatoxin $B_1$, $B_2$, $G_1$ or $G_2$.

The quantity of aflatoxin bound to immunoaffinity columns does not need to be as large as that of RALs since aflatoxins may be detected at much lower levels than RALs. The next section shows how these immunoaffinity columns were used to extract derivatives of fungal metabolites from two high added value products.

C The Use of Small Organic Molecules to Identify Products

Figures 3A, 3B:
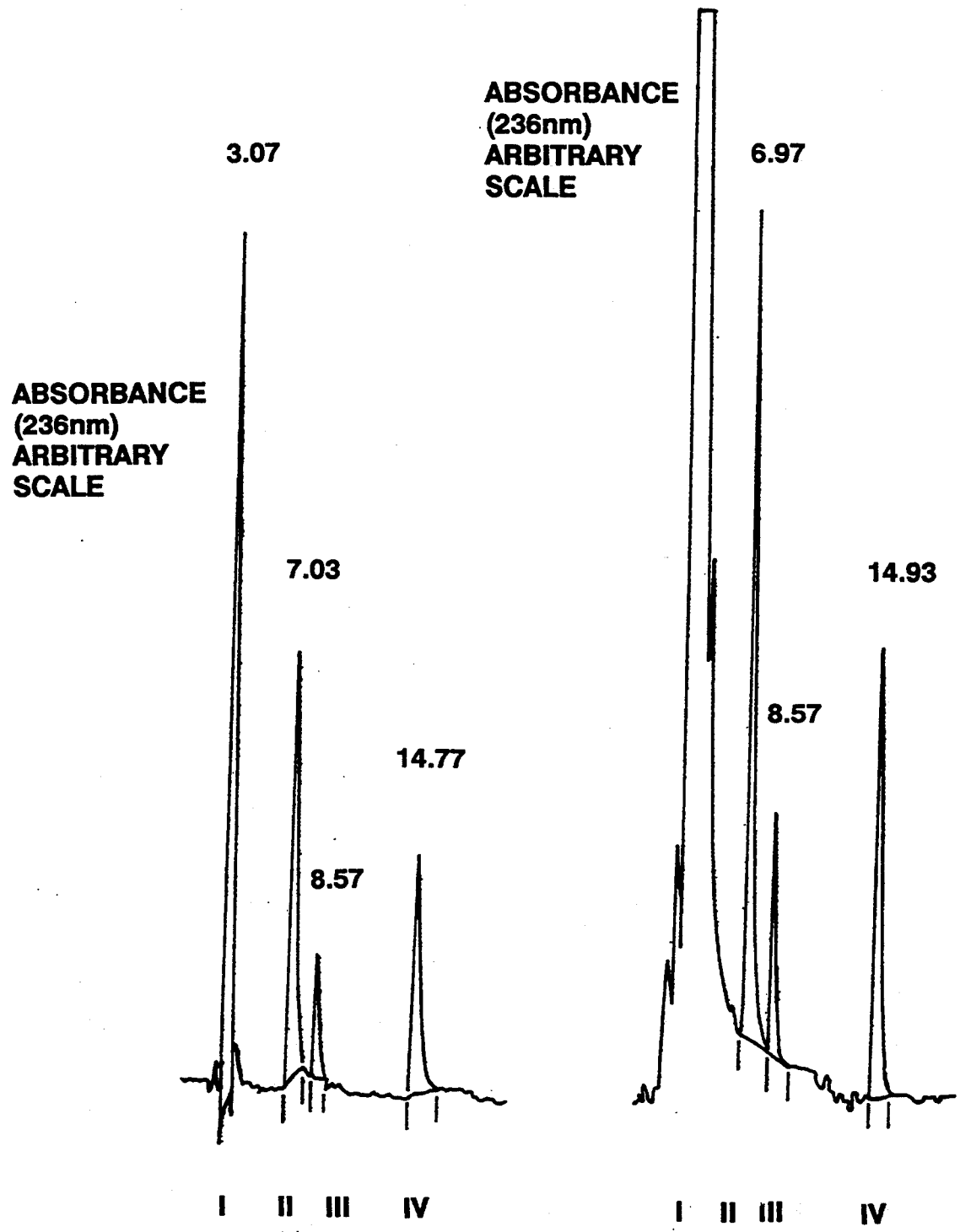
FIG. 3A depicts the socratic elution profile of 25 $\mu$l of a standard solution containing 200 ng/ml of each of zearalenol (ii), zearalanol (iii) and zearalenone (iv).
FIG. 3B depicts the elution profile of the compounds of FIG. 3A after extraction from paracetamol.

Three RALs (400 ng/g) and two aflatoxins (20 ng/g) spiked into paracetamol tablets in different combinations were extracted with greater than 70% efficiency from this pharmaceutical, (Table 1). Each fungal metabolite was quantified from the mean of three sample determinations of peak area compared with peak areas of standard solutions chromatographed before and after the samples. For example, FIG. 3A shows the socratic elution profile of 250 μl of a standard solution containing 200 ng/ml of each of zearalenol (ii), zearalanol (iii) and zearalenone (iv). FIG. 3B shows the elution profile of the RALs after extraction from paracetamol as described in section D (i) above. Some polar material (peak (i)) contaminates the extract, however, this is of no relevance since it does not interfere with quantification of RALs. Retention times (minutes) are given at the top of integrated peaks. Different combinations of RALs and aflatoxins used as spikes can therefore be used to distinguish between different batches of products. Extraction of these fungal metabolites occurred in two phases.

Phase 1. The success of the initial solvent extraction from paracetamol was dependent not only on the solubility of the fungal metabolite in the 30% (v/v) acetonitrile: water but also on the solubility of other chemical constituents of paracetamol. Extraction in this phase was found to be optima in 30% (v/v) acetonitrile: water when compared with 10, 50 and 70% (v/v).

Phase 2. The second phase of extraction involved application of the first extract to the immunoaffinity column. First the solvent was diluted in aqueous solution to a level at which antibodies were able to bind antigen (as organic solvents destroy this ability). Solubility of the fungal metabolite at this stage affects its binding to the immunoaffinity column.

Aflatoxin extracts were diluted to less than 2.5% (v/v) acetonitrile: PBS and RAL extracts to less than 10% (v/v) acetonitrile: water prior to application to the columns.

The efficiency of the eluent for removal of the antigen from the immunoaffinity resin is again dependent on the solubility of the antigen in the eluent, but also on the ability of the eluent to denature the antibody. The latter is dependent on a host of effects. Probably the most important of these effects are factors affecting hydration of the antibody in the eluent solution. The optimum eluent was found to be 100% acetonitrile. This gave satisfactory recoveries of both RALs and aflatoxins and could be diluted to 50% (v/v) acetonitrile in HPLC water for direct quantification by HPLC.

It is likely that the nature of extraction solvents and eluent solvents would be dependent on the nature of the chemicals chosen for spiking individual substrates. However, the results described here show that it is possible to add low concentrations of small organic molecules to pharmaceutical products and to use immunoaffinity chromatography to identify and distinguish between batches of the product.

D The use of Amino Acids as Building Blocks

As an extension of the ability to use small organic molecules for the purpose of identifying and distinguishing between batches of high added value products it is possible to conjugate numbers of different amino acids to a given small organic molecule to which antibodies have been made. While this does not alter the immunoaffinity chromatography of these conjugated small organic molecules it renders them more easily separable by a detection method such a HPLC. Indeed, by HPLC, different amino acid(s) and/or different sequences of the same amino acids could be easily separated. The number of possible combinations is very large as there are 20 natural amino acids and many synthetic chemicals which can be used in such a process. Selection of conjugates depends on their solubility in the solvents used for immunoaffinity chromatography as described in section C of "Results and Discussion".

As a model for this procedure, the applicants have conjugated N-acetyl-lysine to aflatoxin $B_1$ and investigated the conditions for extraction of this from aftershave using immunoaffinity columns directed against aflatoxin. The conjugation was performed as in section A (i) of "Materials and Methods" and confirmed as N-acetyl-L-lyisine aflatoxin $B_1$ spectrophotometrically. This conjugate is readily extractable from liquid cosmetics. For example, Aramis aftershave (500 ul) spiked with N-acetyl-L-lysine aflatoxin $B_1$ (500 ng) was either (a) rotary evaporated or (b) diluted to 1% (v/v) with PBS to lower the alcohol content of this product. This allowed the immunoaffinity column to bind the conjugate which was selectively eluted by applying 67% (v/v) acetonitrile: HPLC grade water to the column. Acetonitrile (non-aqueous) is not an effective eluent and gave very poor yield since the conjugate is less soluble in this than in aqueous acetonitrile.

Figure 4A:
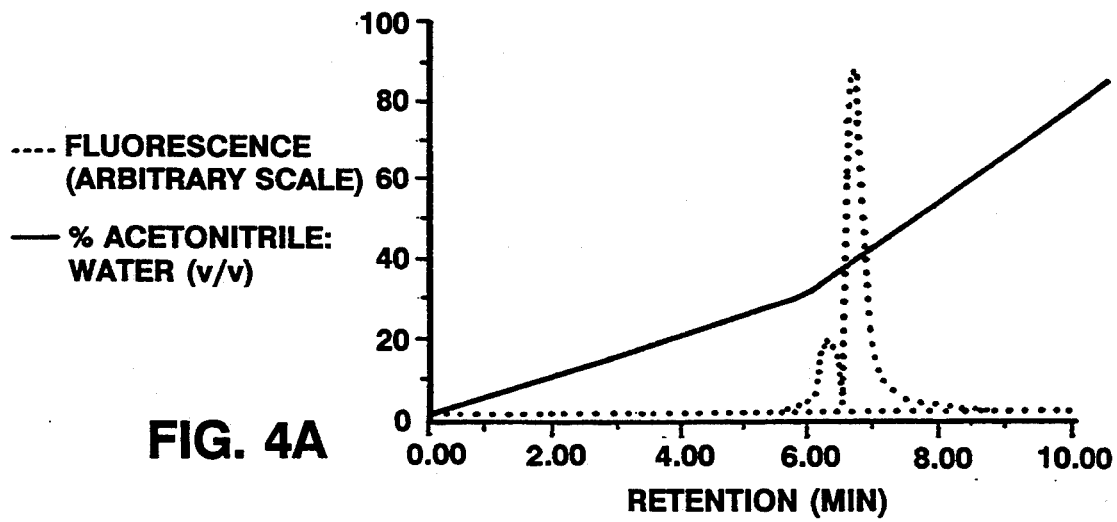
FIG. 4A depicts the elution profile of N-acetyl-L-lysine aflatoxin $B^1$ (250 $\mu$l of 300 ng/ml).
Figure 4B:
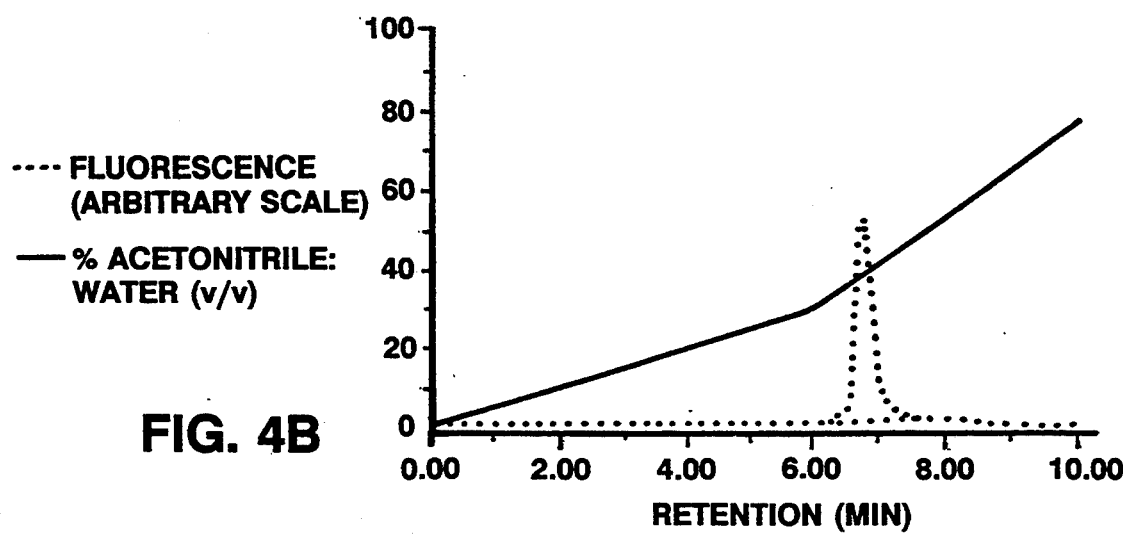
FIG. 4B and 4C depict the elution profiles of n-acetyl-L-lysine aflatoxin $B_1$ as extracted from aftershave by two different methods.
Figure 4C:
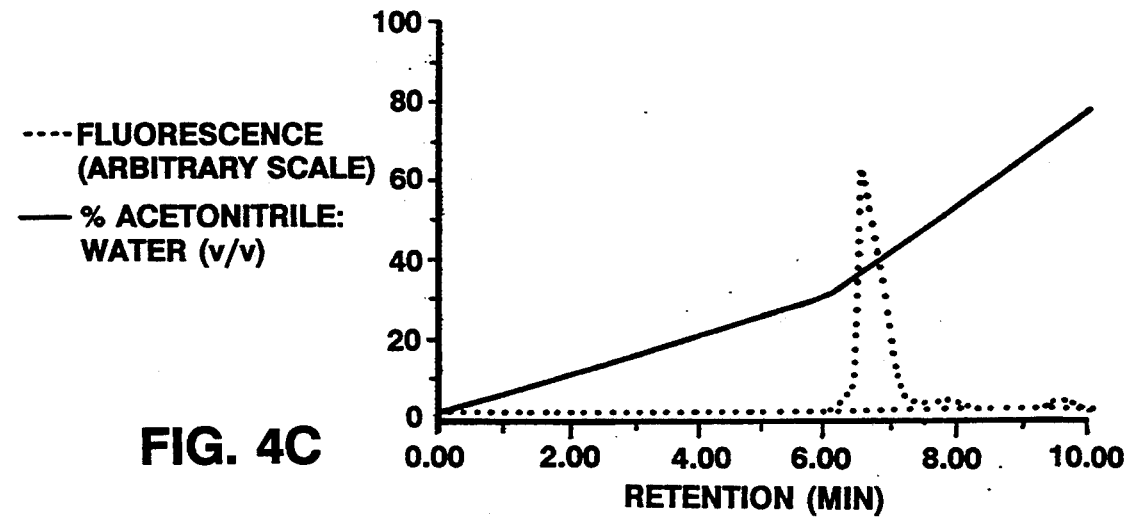

FIG. 4 shows the elution profile of N-acetyl-L-lysine-aflatoxin $B_1$ (250 ul of 300 ng/ml) prepared as in section A (i) of "Materials and Methods" and chromatographed under conditions as described in section D (iii) of "Materials and Methods". The elution gradient (y-axis) is overlaid on the profile, with elution time in minutes on the X-axis. FIG. 4B shows the result of using method A (section D (iii) of "Materials and Methods") for extraction from Aramis aftershave (i.e., initial rotary evaporation to remove alcohol). Had the extraction been 100% efficient this sample would contain 242 ng/ml of N-acetyl-L-lysine-aflatoxin $B_1$. The actual efficiency was 79%. FIG. 4C shows the result of using method B (section D (iii) of "Materials and Methods") for extraction from Aramis (i.e., direct dilution of aftershave). Had the extraction been 100% efficient this sample would contain 325 ng/ml of N-acetyl-L-lysine aflatoxin $B_1$. The actual efficiency was 73%. Aramis which did not contain the N-acetyl-L-lysine aflatoxin $B_1$ marker showed no chromatographed peak during elution.

REFERENCE LIST

1. Sabboni G., Skipper P. L., Buchi G., Tannenbaum S. R. (1987). Isolation and Characterization of the Major Serum Albumin Adduct Formed by Aflatoxin $B_1$ in vivo in rats. Carcinogenesis, 8 (6), 819–824.
2. Thouvenot D. and Morfin R. F. (1983). Radioimmunoassay for Zearalenone and Zearalenol in Human Serum. Applied Environ. Microbiol., 45 (1), 16–23.
3. Voller A., Bidwell D. E., Bartlett A. (1979). The Enzyme Linked Immunosorbent Assay (ELISA). A Guide With Abstracts of Microplate Applications Available From Dynatech Europe, Borough Hosue, Rue du Pre, Guernsey.

Other embodiments are within the scope of the following claims.

What is claimed is:

1. A method of marking a product and subsequently detecting the marker in the product as a means of identifying the product comprising the steps of:
   associating a hapten as a marker with the product, wherein the hapten is non-deleterious to the product, inert with respect to the product, and not already associated with the product; and
   detecting the hapten in the product at a later point in time as a means of identifying the product by specifically binding the hapten to a complementary binding member.

2. The method of claim 1 in which said hapten marker is added directly to said product.

3. The method of claim 2 in which said hapten marker is mixed with said product.

4. The method of claim 3 in which said product is a liquid.

5. The method of claim 4 in which said product is a petroleum product.

6. The method of claim 2 in which said product is a solid and said hapten is applied to the surface of the product.

7. The method of claim 1 in which said hapten marker is added or attached to a tag or packaging associated with said product.

8. The method of claim 1 in which said hapten marker is m-phenoxybenzoic acid.

9. The method of claim 1 wherein said complementary binding member is an antibody to said hapten.

10. A marked product comprising:
    (a) a commercial petroleum product having mixed with it
    (b) a hapten marker not normally associated with said petroleum product.

* * * * *

UNITED STATES PATENT AND TRADEMARK OFFICE
CERTIFICATE OF CORRECTION

PATENT NO. : 5,429,952

DATED : July 4, 1995

INVENTOR(S) : Ronald C. Garner, Carl N. Martin, Michael J. Wraith, and David W. Britton It is certified that error appears in the above-identified patent and that said Letters Patent is hereby corrected as shown below:

Column 2, line 13, replace "Which" with --which--;

Column 2, line 19, replace "inconvenient for, for example," with --inconvenient, for example,--;

Column 8, line 7, replace "15 quantities" with --quantities--;

Column 11, line 43, replace "inoculated" with --innoculated--;

Column 15, line 25, replace "a ml glass bottle" with --a 20 ml glass bottle--;

Column 19, line 12, replace "inoculation" with --innoculation--;

Column 19, line 22, replace "inoculation" with --innoculation--;

Column 19, line 34, replace "Inoculation of mice" with --Innoculation of mice--;

UNITED STATES PATENT AND TRADEMARK OFFICE
CERTIFICATE OF CORRECTION

PATENT NO.  : 5,429,952

DATED       : July 4, 1995

INVENTOR(S) : Ronald C. Garner, Carl N. Martin, Michael J. Wraith, and David W. Britton It is certified that error appears in the above-identified patent and that said Letters Patent is hereby corrected as shown below:

Column 19, line 38, replace "inoculated" with --innoculated--;

Column 19, line 40, replace "inoculated" with --innoculated--;

Column 19, line 41, replace "inoculation" with --innoculation--;

Column 19, line 50, replace "foetal" with --fetal--;

Columns 21-22, TABLE 8, replace "0" with --100-- as shown by the circle in red below:

TABLE 8

| | EXTRACTION OF SMALL ORGANIC MOLECULES PRO PARACETAMOL | | | | | | | | | | | | | | |
|---|---|---|---|---|---|---|---|---|---|---|---|---|---|---|---|
| | ZEARALENOL | | | ZEARALANOL | | | ZEARALENONE | | | AFLATOXIN $G_1$ | | | AFLATOXIN $G_2$ | | |
| | Amount Added ng/g | Amount Recovered ng/g | % Recovery | Amount Added ng/g | Amount Recovered ng/g | % Recovery | Amount Added ng/g | Amount Recovered ng/g | % Recovery | Amount Added ng/g | Amount Recovered ng/g | % Recovery | Amount Added ng/g | Amount Recovered ng/g | % Recovery |
| 1 | 400 | 344 | 86 | 400 | 340 | 85 | 400 | 356 | 89 | 0 | 0 | 0 | 0 | 0 | 0 |
| 2 | 400 | 280 | 70 | 0 | 0 | 0 | 400 | 380 | 95 | 0 | 0 | 0 | 0 | 0 | 0 |
| 3 | 400 | 288 | 72 | 400 | 404 | 101 | 0 | 0 | 0 | 0 | 0 | 0 | 0 | 0 | 0 |
| 4 | 0 | 0 | 0 | 400 | 396 | 99 | 400 | 412 | 103 | 0 | 0 | 0 | 0 | 0 | 0 |
| 5 | 0 | 0 | 0 | 0 | 0 | 0 | 400 | 388 | 97 | 0 | 0 | 0 | 0 | 0 | 0 |
| 6 | 400 | 356 | 89 | 0 | 0 | 0 | 0 | 0 | 0 | 0 | 0 | 0 | 0 | 0 | 0 |
| 7 | 0 | 0 | 0 | 400 | 320 | 80 | 0 | 0 | 0 | 0 | 0 | 0 | 0 | 0 | 0 |
| 8 | 0 | 0 | 0 | 400 | 320 | 80 | 400 | 400 | 100 | 0 | 0 | 0 | 0 | 0 | 0 |
| 9 | 0 | 0 | 0 | 0 | 0 | 0 | 0 | 0 | 0 | 20 | 15.5 | 76.3 | 20 | 16 | 80.0 |

UNITED STATES PATENT AND TRADEMARK OFFICE
CERTIFICATE OF CORRECTION

PATENT NO. : 5,429,952
DATED : July 4, 1995
INVENTOR(S) : Ronald C. Garner, Carl N. Martin, Michael J. Wraith, and David W. Britton It is certified that error appears in the above-indentified patent and that said Letters Patent is hereby corrected as shown below:

Column 23, line 55, replace "lyisine" with --lysine--.

Signed and Sealed this

Third Day of October, 1995

Attest:

BRUCE LEHMAN

Attesting Officer        Commissioner of Patents and Trademarks